(12) United States Patent
Shibuya

(10) Patent No.: US 7,553,870 B2
(45) Date of Patent: Jun. 30, 2009

(54) USE OF POLYUNSATURATED FATTY ACID FOR THE PRIMARY PREVENTION OF MAJOR CARDIOVASCULAR EVENTS

(75) Inventor: Hajime Shibuya, Komae (JP)

(73) Assignee: Pro Aparts Investimentos E Consultoria LDA, Madeira (PT)

( * ) Notice: Subject to any disclaimer, the term of this patent is extended or adjusted under 35 U.S.C. 154(b) by 687 days.

(21) Appl. No.: 10/778,182

(22) Filed: Feb. 17, 2004

(65) Prior Publication Data

US 2004/0162349 A1 Aug. 19, 2004

Related U.S. Application Data

(62) Division of application No. 10/281,208, filed on Oct. 28, 2002, now abandoned.

(30) Foreign Application Priority Data

Nov. 12, 2001 (IT) .......................... MI2001A2384

(51) Int. Cl.
*A61K 31/22* (2006.01)
*A61K 31/20* (2006.01)
*A61K 35/60* (2006.01)
(52) U.S. Cl. .................. 514/549; 514/560; 424/523
(58) Field of Classification Search ................. 514/549, 514/560
See application file for complete search history.

(56) References Cited

U.S. PATENT DOCUMENTS

| | | | |
|---|---|---|---|
| 5,130,061 A | 7/1992 | Cornieri et al. ............. 554/167 |
| 5,378,732 A | 1/1995 | Horrobin et al. ............ 514/560 |
| 5,502,077 A | 3/1996 | Breivik et al. ............... 514/560 |
| 5,541,225 A | 7/1996 | Leaf et al. ................... 514/560 |
| 5,656,667 A | 8/1997 | Breivik et al. ............... 514/560 |
| 5,698,594 A | 12/1997 | Breivik et al. | |
| 5,753,703 A | 5/1998 | Cavazza et al. ............. 514/556 |
| 5,760,081 A | 6/1998 | Leaf et al. | |
| 5,776,978 A | 7/1998 | Burzzese | |
| 5,859,055 A | 1/1999 | Horrobin et al. ............ 514/549 |
| 5,869,714 A | 2/1999 | Bruzzese | |
| 6,008,248 A | 12/1999 | Pscherer et al. ............. 514/560 |
| 6,245,811 B1 | 6/2001 | Horrobin et al. | |
| 6,284,268 B1 | 9/2001 | Mishra et al. ................ 424/455 |
| 6,670,396 B2 * | 12/2003 | Serhan et al. ................ 514/549 |
| 2003/0144219 A1 | 7/2003 | Phinney et al. ................ 514/27 |
| 2008/0269331 A1 | 10/2008 | Shibuya ....................... 514/560 |

FOREIGN PATENT DOCUMENTS

| | | |
|---|---|---|
| CN | 1082909 A | 0/1993 |
| EP | 0409903 B1 | 4/1992 |
| EP | 0 780 124 | 6/1997 |
| EP | 1 157 692 | 11/2001 |
| EP | 1157692 B1 | 10/2005 |
| JP | 02/25447 | 7/1988 |
| WO | WO89/11521 | 11/1989 |
| WO | WO 00/32210 | 6/2000 |
| WO | WO00/48592 | 8/2000 |
| WO | WO 01/46115 A1 | 6/2001 |
| WO | WO 01/60778 | 8/2001 |
| WO | WO02/058793 | 8/2002 |
| WO | WO 2008/066745 A1 | 6/2008 |

OTHER PUBLICATIONS

Harrison's Principles of Internal Medicine, 13th Ed., vol. 1, published 1994 by McGraw-Hill, Inc. (NY), pp. 1108-1116.*
The Merck Manual of Diagnosis and Therapy, 14th Ed., published 1982 by Merck, Sharp & Dohme Research Laboratories (NJ), pp. 386-389 and 1036-1053.*
R. Pakala, et al., Atherosclerosis 153, XP-002229283, pp. 47-57, "Vascular Smooth Muscle Cells Preloaded With Eicosapentaenoic Acid and Docosahexaenoic Acid Fail to Respond to Serotonin Stimulation", 2000.
S. Takeo, et al., Molecular and Cellular Biochemistry 188, XP-008012809, pp. 199-208, "Effects of Long-Term Treatment With Eicosapentaenoic Acid on the Heart Subjected to Ischemia/Reperfusion and Hypoxia/Reoxygenation in Rats", 1998.
R. B. Singh, et al., Cardiovascular Drugs and Therapy 11, XP-008012824, pp. 485-491, "Randomized, Double-Blind, Placebo-Controlled Trial of Fish Oil and Mustard Oil in Patients With Suspected Acute Myocardial Infarction: The Indian Experiment of Infact Survival", 1997.
E. Guallar, et al., Arteriosclerosis, Thrombosis, and Vascular Biology 19, XP-001134928, pp. 1111-1118, "Omega-3 Fatty Acids in Adipose Tissue and Risk of Myocardial Infarction: the Euramic Study", 1999.
P. McLennan, et al., European Journal of Pharmacology 300, XP-001134929, pp. 83-89, The Cardiovascular Protective Role of Docosahexaenoic Acid, 1996.
T. Rissanen, et al., Circulation, vol. 102, No. 22, XP-001134935, pp. 2677-2679, "Fish Oil-Derived Fatty Acids, Docosahexaenoic Acid and Docosapentaenoic Acid, and the Risk of Acute Coronary Events", Nov. 28, 2000.
T. H. Rissanen, et al., Circulation, vol. 98, No. 17, XP-008012807, p. 2823, "Fish Oil-Derived Fatty Acids, Docosahexaenoic Acid and Docosapentaenoic Acid, and the Risk of Acute Myocardial Infarction", Oct. 27, 1998.
Jahangiri, et al., "Restoration of Synchronous Contractile Activity by n-3 PUFAs in Atrial Cardiomyocytes", *Journal of Molecular and Cellular Cardiology*, vol. 31, No. 1, A6 (1999).

(Continued)

*Primary Examiner*—Raymond J Henley, III
(74) *Attorney, Agent, or Firm*—Charles M. Kinzig; Alan Scrivner; Loretta J. Sauermelch

(57) ABSTRACT

The use of polyunsaturated fatty acids of the ω-3 series such as eicosapentaenoic acid (EPA, $C_{20:5}$ ω-3), docosahexaenoic acid (DHA, $C_{22:6}$ ω-3), or their pharmaceutically acceptable derivatives is described for the primary prevention of major cardiovascular events in subjects who have not undergone previous infarct episodes.

34 Claims, No Drawings

OTHER PUBLICATIONS

Jahangiri, et al., "Termination of Asynchronous Contractile Activity in Rat Atrial Myocytes by n-3 Polyunsaturated Fatty Acids", *Molecular and Cellular Biochemistry*, vol. 206, pp. 33-41 (Mar. 2000).

J. Kang and A. Leaf, "Protectice effects of free polyunsaturated fatty acids on arrhythmias induced by lysophosphatidylcholine or palmitoylcarnitine in neonatal rat cardiac myocytes," *European Journal of Pharmacology*, vol. 297, No. 1-2, pp. 97-106 (1996).

Maixent, et al., "Remodeling of Na, K-ATPase, and Membrane Fluidity After Atrial Fibrillation in Sheep", *Journal of Receptors and Signal Transduction*, vol. 22, Nos. 1-4, pp. 201-211 (2002; online publication date Jan. 12, 2002).

Siclari, et al., "Long Chain n 3 Fatty Acids Can Prevent Paroxysmal Atrial Fibrillation", *Circulation*, vol. 106, No. 19 Suppl., pp. II 635 (Nov. 5, 2002).

Declaration of Cordelia Slaughter, dated Nov. 28, 2006, regarding Siclari et al., "Long Chain n 3 Fatty Acids Can Prevent Paroxysmal Atrial Fibrillation", Circulation, vol. 106, No. 19 Suppl. pp. II 635.

US2008-0269331 (U.S. Appl. No. 11/984,485), Office Action dated Dec. 24, 2008 (7 total pages).

EP 1157692B1 Notice of Opposition by IBSA Institut Biochimique S.A., Jul. 5, 2006, pp. 1-12 (e.g., pp. 9-10, section C).

EP 1157692B1 Notice of Opposition by Pronova Biocare A.S., Jul. 5, 2006, pp. 1-24 (e.g., p. 22, section 3.17).

EP 1157692B1 Contestment of Opposition by Pro Aparts-Investimentos e Consultoria LDA, Apr. 11, 2007, pp. 1-24 and Annex 1 pp. 1-7, Annex 2, pp. 1-7, Annex 3 pp. 1-7, Annex 4 pp. 1-7 (e.g., p. 3 section 5; p. 15 section 9.3; pp. 23-24, section 9.4.8).

L. Frost et al.; n-3 Fatty acids consumed from fish and risk of atrial fibrillation or flutter: the Danish Diet, Cancer, and Health Study; Am J Clin Nutr 2005; 81:50-4.

D. Mozaffarian et al.; Fish intake and risk of incident atrial fibrillation; Circulation 2004; Jul. 27; 110(4):368-73.

Swann et al., Clinical Drug Investigation 15 (6), 473-482, 1998.

\* cited by examiner

USE OF POLYUNSATURATED FATTY ACID FOR THE PRIMARY PREVENTION OF MAJOR CARDIOVASCULAR EVENTS

CROSS-REFERENCE TO RELATED APPLICATIONS

The present application is a divisional of application Ser. No. 10/281,208, filed Oct. 28, 2002, now abandoned.

The invention relates to the use of polyunsaturated fatty acids for the primary prevention of major cardiovascular events.

In particular, the invention concerns the use of polyunsaturated fatty acids of the ω-3 series such as eicosapentaenoic acid (EPA, $C_{20:5}$ ω-3), docosahexaenoic acid (DHA, $C_{22:6}$ ω-3), or their pharmaceutically acceptable derivatives, either alone or mixed together, for the primary prevention of major cardiovascular events.

The beneficial effects of polyunsaturated fatty acids of the ω-3 series on multiple risk factors for cardiovascular illnesses are well known; for example the patents IT 1235879, U.S. Pat. No. 5,502,077, U.S. Pat. No. 5,656,667 and U.S. Pat. No. 5,698,594 refer respectively to hypertriglyceridemia, defects of the cholesterol level and hypertension. However, each of the cited documents deal with the treatment of risk factors, not with real and proclaimed illnesses.

U.S. Pat. No. 5,753,703 describes the use of L-carnitine or its derivatives in association with polyunsaturated fatty acids of the ω-3 series or their esters, in particular EPA and DHA, for the prevention and treatment of cardiovascular disorders, vascular pathologies, diabetic peripheral neuropathies, and atherosclerotic, thromboembolytic and tissue disorders.

EP-B-0409903 describes a process for preparing high concentration mixtures of EPA and DHA and/or their esters useful for treating hyperlipemia and related pathologies, thrombosis, cardiac infarct, platelet aggregation, as anticoagulants in the prevention of atherosclerosis, for the treatment of cerebral infarct, of lesions and occlusions caused by vasomotor spasms, of diabetes and its complications, of chronic and acute inflammations, of autoimmune symptoms, in the prevention of side effects caused by non-steroid anti-inflammatories at the gastrointestinal level and in tumour prevention.

CN 1082909 describes compositions based on ethyl esters of EPA and DHA and other polyunsaturated fatty acids of the ω-3 series in association with soya phospholipids, oenothera odorata and ginkgetin, as antithrombotic and antidementia agents for treating for example dementia and infarct of the myocardium.

U.S. Pat. No. 5,760,081 describes a method for preventing imminent fibrillation of the myocardial ventricle by intravenous infusion of a composition containing EPA, where the subject at risk of imminent fibrillation has already often been the protagonist of an episode of infarct of the myocardium and where the infusion is effected within 3 hours of the infarct episode, possibly using intracardiac injection. These are always situations of extreme emergency and of parenteral intervention, for the specific treatment of ventricular fibrillation.

Swann et al., Clinical Drug Investigation 15 (6), 473, 1998 have also shown that the administration of EPA and DHA ethylesters, at a dose of 4 g per day, leads to a decrease in triglycerides and total apolipoprotein C III and to an increase in antithrombin III, in subjects with abnormal plasmatic lipoprotein symptoms and have undergone an infarct of the myocardium, they having consequently suggested that an administration of these compositions can result in an improvement in the lipoprotein level and hence a decrease in the relative risk factors.

WO 00/48592 describes the use of a mixture of EPA and DHA ethylesters in quantities greater than 25 wt. % for preventing death, in particular "sudden death" in patients who have already suffered an infarct of the myocardium. This therefore represents the use of said mixture in so-called secondary death prevention, i.e. in subjects who have already suffered infarct.

The prevention of cardiovascular damage by means of fatty acid mixtures described in the state of the art is therefore focused on "secondary" prevention of cardiovascular damage. i.e. aimed at protecting a subject who has already suffered an infarct, whereas "primary" prevention of major cardiovascular events, i.e. prevention in subjects who, while affected by various pathologies of the cardiocirculatory and/or cardiorespiratory systems, have not yet suffered an infarct episode, constitutes a technical problem which is still felt in this sector.

According to a first aspect the invention relates to the use of polyunsaturated fatty acids of the ω-3 series for the preparation of a drug useful in the primary prevention of a major cardiovascular event in subjects who have not undergone previous infarct episodes, wherein the fatty acids comprise eicosapentaenoic acid (EPA) and/or docosahexaenoic acid (DHA) and/or at least one pharmaceutically acceptable derivative thereof, in quantities greater than or equal to 25 wt % on the total fatty acid weight.

In the present description, the expression "polyunsaturated fatty acids of the ω-3 series" means those long-chain polyunsaturated fatty acids, generally $C_{16}$-$C_{24}$, containing fish oils, in particular those having a $C_{20}$-$C_{22}$ chain, which are predominant in purification processes.

The expression "major cardiovascular event" means in particular those events which involve reversible or irreversible cardiovascular damage, such as infarct of the myocardium and of individual coronary branches, death from cardiac causes, sudden death, etc., besides to infarct, broadly speaking, ictus etc., and those conditions prodromal to such major events, such as myocardial fibrillation, atrial and/or ventricular fibrillation, etc. Said major cardiovascular events are usually induced by various cardiocirculatory and cardiorespiratory pathologies such as coronary ischemic illness not displayed by previous infarct episodes, and by serious hypoxic/anoxic states caused by a sudden lack of oxygen (for example during anesthesia, surgery, etc.), possibly in the presence of conditions which contemplate an increase in the oxygen requirement. (accentuated physical stress, drug abuse, acute hypertensive crises, etc.) and analogous acute and chronic pathologies due to cardiac defects of electrical and/or mechanical type.

The subjects affected by pathologies of the cardiocirculatory and cardiorespiratory system, hence not simply at prospective risk due to hypertriglyceridemia, hypertension or other, are representative of subjects definable at various levels as cardiopaths, by being affected, for example, by coronary ischemia detectable by coronarography, scintigraphy of the myocardium, electrocardiogram (ECG) under stress, etc., against which interventions of revascularization (angioplasty) or other possible pharmacological or invasive treatments have been proposed, and of subjects affected by electrical hyperexcitability of the myocardium cells, disorder of the diffusion of electrical excitement or of electrical conduction (arrhythmia, fibrillation, etc.) or by other defects of mechanical type (cardiac insufficiency, decompensation), possibly aggravated by concomitant pathologies such as diabetes.

The use of polyunsaturated fatty acids of the ω-3 series according to the invention is particularly indicated if the occurrence of a major event is predicted, such as an infarct, in particular of the myocardium, death from a cardiological cause, or sudden death, and where such an occurrence takes place in cardiopathic subjects affected, for example, by coronary ischemia, arrhythmia, atrial and/or ventricular fibrillation, electrical hyperexcitability of the myocardium cells, disorder of the diffusion of electrical excitement or of electrical conduction of the myocardium, or cardiac disorders of mechanical type, for example cardiac insufficiency or cardiac decompensation, possibly affected by diabetic pathology concomitant with the cardiopathy.

Preferably, the content of EPA and/or DHA and/or of the at least one derivative thereof is between 50% and 100%, in particular between 75% and 95%, and more preferably about 85% by weight on the total fatty acid weight. The preferred EPA and/or DHA derivatives are selected from the corresponding $C_1$-$C_3$ alkyl esters and/or from their salts with pharmaceutically acceptable bases such as sodium hydroxide, lysine, arginine or aminoalcohols such as choline. The ethylesters of EPA and DHA, in particular mixed together in any concentration and percentage, are the most preferred.

The drug is administered preferably orally, in particular in the form of soft gelatin capsules. For oral use, the unit dose generally comprises 100-1000 mg of polyunsaturated fatty acids of the ω-3 series, preferably 500-1000 mg or 300-500 mg, the total dose being usually around 0.1-3.0 g per day or per alternate day, according to the case concerned, and preferably 0.3-2.0 g per day and in particular 1.0 g per day. The effective dose of the drug suitable for the use of the invention is 1.0-60.0 mg/kg of body weight/day.

Other types of formulation for oral administration are also suitable for the purposes of the invention; for example hard capsules or tablets, in which the polyunsaturated fatty acids are adsorbed on solid supports. It is also possible to use emulsions, granulates in dispersing excipients, syrups, droplets, etc., and other forms of administration able to ensure systemic absorption of the drug, such as sterile solutions or emulsions and the like, suitable for parenteral use and the like, as evaluated by the expert of the art, on the basis of the severity of the pathology.

Those compositions illustrated in the European Pharmacopea 2000 (EuPh. 2000), containing quantities greater than or equal to 80 wt % of mixtures of EPA and DHA ethylesters and a total of ω-3 polyunsaturated fatty acid ethylesters greater than or equal to 90 wt % are also suitable for the purposes of the present invention.

The aforestated compositions and the drugs suitable for the use of the invention can be prepared by methods known to the expert of the art, such as those described in U.S. Pat. No. 5,130,061, WO 89/11521, IT 1235879, JP 02/25447, which are incorporated into the present description with regard to the method of preparation.

The drug suitable for use according to the present invention can also comprise other active principles and/or drugs, in association, possessing activity complementary to or synergic with that of the drug suitable for use according to the invention, and also at least one pharmaceutically acceptable vehicle and/or one diluent and/or one surfactant and/or one thickener and/or one binder and/or one lubricant and/or one aromatizer and/or one colorant and/or one stabilizer and the like, which can easily be selected by the expert of the art. Of the stabilizers, antioxidants such as vitamin E (tocopherol), ascorbyl palmitate, ascorbic acid, hydroxytoluene and the like, which can be easily selected by the expert of the art, are particularly preferred.

According to another aspect, the invention relates to a method for the primary prevention of a major cardiovascular event in subjects who have not undergone previous infarct episodes, comprising the administration of an effective dose of a drug comprising polyunsaturated fatty acids of the ω-3 series as hereinbefore described. In particular, the method of the invention is indicated whenever the occurrence of a major cardiac event is predicted such as an infarct, in particular of the myocardium, death from a cardiological cause or sudden death.

The following examples illustrate the invention but without limiting it.

The compositions illustrated in the following table were prepared by the methods described in U.S. Pat. No. 5,130,061 (compositions A, C, D, F), IT 1235879 (composition B), JP 02/25447 (composition E) and WO 89/11521 (compositions G-1).

All the quantities indicated in the following table express percentages by weight on the total weight of polyunsaturated fatty acids of the ω-3 series.

|  | $A^1$ | $B^1$ | $C^1$ | $D^1$ | $E^1$ | $F^1$ | $G^1$ | $H^2$ | $I^3$ |
|---|---|---|---|---|---|---|---|---|---|
| EPA | >40 | >44 | >40 | >25 | >80 | >20 | <15 | >40 | >40 |
| DHA | >34 | >30 | >34 | >20 | <10 | >25 | >80 | >30 | >30 |
| EPA + DHA | >85 | >80 | >80 | >50 | >80 | >50 | >85 | >80 | >80 |
| esters[4] tot. |  | >3 | — |  |  |  |  |  |  |
| esters[5] |  |  | >90 |  |  |  |  |  |  |
| α-tocopherol | 0.03 | 0.03 | 0.1 | 0.3 | 0.1 | 0.3 | 0.03 | 0.1 | 0.1 |

[1] ethyl esters;
[2] free acids;
[3] sodium salts;
[4] ethyl esters of other ($C_{20}$, $C_{21}$, $C_{22}$) ω-3 acids;
[5] total ethyl esters of ω-3 acids.

EXAMPLE 2

The compositions illustrated in the following table, relative to soft gelatin capsules containing 1 g of polyunsaturated fatty acid ethyl esters, were prepared by methods known in the art.

|  | A (mg) | B (mg) | C (mg) |
|---|---|---|---|
| EPA[1] | 525 | — | >400 |
| DHA[1] | 315 | — | >340 |
| EPA + DHA[1] |  | 850 | >800 |
| Total ω-3[1] |  | — | >900 |
| d-α-tocopherol | 4 I.U. | — | 4 I.U. |
| d,l-α-tocopherol |  | 0.3 |  |
| gelatin | 246 | — | 246 |
| gelatin succinate |  | 233 |  |
| glycerol | 118 | 67 | 118 |
| OFR | 2.27 | — | 2.27 |
| OFG | 1.27 |  | 1.27 |
| SOB |  | 1.09 |  |
| SPOB |  | 0.54 |  |

[1] ethyl esters;
OFR: red iron oxide
OFG: yellow iron oxide;
SOB: sodium p-oxybenzoate;
SPOB: sodium propyl p-oxybenzoate;
I.U.: international units.

Pharmacological Activity

The pharmacological activity of the compositions of the invention was evaluated on the basis of tests carried out on small laboratory animals (mouse, guinea pig, rat); this experimental model was chosen because of the ability to make rapid and highly reproducible verifications and to use a sufficiently large number of animals, such as to enable a statistically accurate evaluation of the results to be made without exposing the patient to risk, with evident ethical implications.

During the course of these tests, groups of animals were pretreated repeatedly with the formulations of Examples 1 and 2 and then, in comparison with untreated groups, were subjected to the action of cardiotoxic or respiration-depressive substances, then visually measuring protection against death, or—by means of elettrocardiographic recording—measuring the delay in the start of initial cardiac arrhythmia or of ventricular tachycardia and above all the delay in or the prevention of animal death due to sudden cardiac and/or respiratory arrest.

Using an analogous experimental model, cardiological pathology, coronary ischemia and a state of infarct were induced by coronary ligature instead of by cardiotoxic agents.

Test 1

The experimental sudden death model was obtained by cardiac arrest induced by intravenous (i.v.) administration of a cardiotoxic agent (ouabain). In preliminary tests, various doses of ouabain were administered to non-anesthetized guinea pigs of both sexes of weight 300-380 g, in order to determine the minimum lethal dose for 100% of the animals within 15 minutes from i.v. injection (240 mg/kg, intravenously administered over 3 minutes).

Two groups of 20 guinea pigs were then treated with 50 and 100 mg/kg of a composition containing 85% of EPA and DHA ethylesters (Ex. 1, composition A) for 10 days. After 2 hours from the last administration the two groups of guinea pigs and a further untreated group, used as control, were treated with 240 mg/kg i.v. of ouabain, recording mortality within the subsequent 15 minutes.

Results expressed as survivors after 15 minutes:

Controls 00/20

50 mg/kg 11/20

100 mg/kg 16/20

Test 2

3 groups of 15 male mice, initial weight 25-32 g, were treated orally for 15 days with physiological solution (control group) and with 50 or 100 mg/kg of a composition containing 85% of EPA and DHA ethylesters (Ex. 1, composition A).

60 minutes after the end of the last treatment, the animals of all the groups were treated with sodium pentabarbital i.p. (50 mg/kg) and then with aconitine i.v. (0.25 mg/kg). The times of appearance of cardiac arrhythmia (deviation >5 seconds from the normal sinus rhythm), of ventricular fibrillation and of cardiac arrest were determined by electrocardiograph recording. Results expressed as mean±standard deviation (seconds) on the positive animals.

| T | $t_1$ (sec) | $t_2$ (sec) | $t_3$ (sec) | S |
|---|---|---|---|---|
| C | 123 ± 12 (15/15) | 174 ± 7 (15/15) | 214 ± 32 (15/15) | 00/15 |
| 50 mg/kg | 168 ± 8 (08/15) | 235 ± 16 (06/15) | 350 ± 26 (06/15) | 09/15 |
| 100 mg/kg | 195 ± 15 (05/15) | 284 ± 18 (03/15) | 378 ± 35 (03/15) | 12/15 |

T-treatment;
$t_1$-time of appearance of arrhythmia (number of animals);
$t_2$-time of appearance of fibrillation (number of animals);
$t_3$-time of cardiac arrest (number of animals);
S-survivors after 15 minutes;
C-control (with physiological solution).

Test 3

2 groups of 20 male rats, initial weight 310-350 g, were treated orally for 15 days with physiological solution (control group) and with 100 mg/kg of a composition containing >80% of EPA and DHA ethylesters (Ex. 1, composition B). The rats of the 2 groups were then anesthetized with sodium pentobarbital i.p. (50 mg/kg), then subjected to ligature of the left anterior descending coronary artery, which allows blood flow to the left ventricle, so inducing an acute ischemic state of the myocardium. During the subsequent 15 minutes the duration of ventricular fibrillation was recorded by ECG, this either resolving itself spontaneously or concluding with sudden death.

Results

| T | F (sec) | Mortality | S (%) |
|---|---|---|---|
| C | 190 ± 24 (18/20) | 16/20 | 20 |
| 100 mg/kg | 55 ± 5 (04/20) | 01/20 | 95 |

T-treatment;
F-duration of fibrillation;
S-survivors after 15 minutes;
C-control (with physiological solution).

Test 4

The experimental model implemented for sudden death by respiratory arrest involves its inducement by chloroform inhalation.

4 groups of 10 male mice, initial weight 26-32 g, were treated orally for 5 days with physiological solution (control group) and with 10, 30 and 60 mg/kg of a composition containing 80% of EPA and DHA ethylesters (Ex. 1, composition C).

60 minutes after the end of the last treatment, the animals were exposed to chloroform until respiratory arrest had occurred. The animals were then checked for tachyarrhythmia of the myocardium induced by the hypoxic state, this either resolving itself spontaneously within the next 15 minutes or concluding with death of the animal.

Results

| Treatment | Protection from tachyarrhythmia | Survivals |
|---|---|---|
| Control | 00/10 | 03/10 |
| 10 mg/kg | 04/10 | 06/10 |
| 30 mg/kg | 07/10 | 08/10 |
| 60 mg/kg | 09/10 | 10/10 |

Test 5

2 groups of 20 male rats were treated as on Test 3, with physiological solution and with the same EPA and DHA composition (Example 1, composition B).

Ligature of the circumflex coronary artery was then effected, with consequent reduction in the contractile capacity of the myocardium and of the ejection fraction. The mortality of 18/20 animals of the control group fell to 4/20 of the treated group, during the course of the subsequent 60 minutes.

The clinical results of the tests demonstrate the pharmacological activity of the polyunsaturated fatty acids of the ω-3 series in the primary prevention of major cardiovascular events in subjects who have not undergone previous infarct episodes.

The invention claimed is:

1. A method of treating atrial fibrillation, comprising administering to a subject in need thereof an effective amount of a pharmaceutical composition comprising ω-3 fatty acids comprising eicosapentaenoic acid (EPA), docosahexaenoic acid (DHA), a $C_1$-$C_3$ alkyl ester thereof, a pharmaceutically acceptable salt thereof, or mixtures thereof, in an amount of at least 25% by weight of total fatty acids.

2. The method of claim 1, wherein the ω-3 fatty acids comprise a mixture of EPA, DHA, a $C_1$-$C_3$ alkyl ester thereof, or a pharmaceutically acceptable salt thereof, in an amount of at least 25% by weight of total fatty acids.

3. The method of claim 1, wherein the ω-3 fatty acids comprise a mixture of EPA ethyl ester and DHA ethyl ester in an amount of at least 25% by weight of total fatty acids.

4. The method of claim 1, wherein the ω-3 fatty acids comprise a mixture of EPA ethyl ester and DHA ethyl ester in an amount of at least 50% by weight of total fatty acids.

5. The method of claim 1, wherein the ω-3 fatty acids comprise ω-3 fatty acid ethyl esters in an amount of at least 90% by weight of total fatty acids, wherein the ω-3 fatty acid ethyl esters includes a mixture of EPA ethyl ester and DHA ethyl ester in an amount of at least 80% by weight of total fatty acids.

6. The method of claim 1, wherein the effective amount is between 1-60 mg/kg of the subject's body weight per day.

7. The method of claim 1, wherein the subject is cardiopathic.

8. The method of claim 1, wherein the subject is affected by coronary ischemia.

9. The method of claim 1, wherein the subject is affected by cardiac insufficiency.

10. The method of claim 1, wherein the subject is affected by cardiac decompensation.

11. The method of claim 1, wherein the subject is affected by diabetic pathology concomitant with cardiopathy.

12. The method of claim 1, wherein the pharmaceutical composition is administered orally.

13. A method of treating atrial fibrillation, comprising administering to a subject in need thereof an effective amount of oral dosage forms comprising 500-1000 mg of ω-3 fatty acids comprising eicosapentaenoic acid (EPA), docosahexaenoic acid (DHA), a $C_1$-$C_3$ alkyl ester thereof, a pharmaceutically acceptable salt thereof, or mixtures thereof, in an amount of at least 25% by weight of total fatty acids.

14. The method of claim 13, wherein the ω-3 fatty acids comprise a mixture of EPA, DHA, a $C_1$-$C_3$ alkyl ester thereof, or a pharmaceutically acceptable salt thereof, in an amount of at least 25% by weight of total fatty acids.

15. The method of claim 13, wherein the ω-3 fatty acids comprise a mixture of EPA ethyl ester and DHA ethyl ester in an amount of at least 25% by weight of total fatty acids.

16. The method of claim 13, wherein the ω-3 fatty acids comprise a mixture of EPA ethyl ester and DHA ethyl ester in an amount of at least 50% by weight of total fatty acids.

17. The method of claim 13, wherein the ω-3 fatty acids comprise ω-3 fatty acid ethyl esters in an amount of at least 90% by weight of total fatty acids, wherein the ω-3 fatty acid ethyl esters includes a mixture of EPA ethyl ester and DHA ethyl ester in an amount of at least 80% by weight of total fatty acids.

18. The method of claim 13, wherein the subject is cardiopathic.

19. The method of claim 13, wherein the subject is affected by coronary ischemia.

20. The method of claim 13, wherein the subject is affected by cardiac insufficiency.

21. The method of claim 13, wherein the subject is affected by cardiac decompensation.

22. The method of claim 13, wherein the subject is affected by diabetic pathology concomitant with cardiopathy.

23. A method of treating atrial fibrillation, comprising orally administering to a subject in need thereof an effective amount of between 1-60 mg/kg of the subject's body weight per day of a pharmaceutical composition comprising ω-3 fatty acids comprising ω-3 fatty acid ethyl esters in an amount of at least 90% by weight of total fatty acids, wherein the ω-3 fatty acid ethyl esters includes a mixture of EPA ethyl ester and DHA ethyl ester in an amount of at least 80% by weight of total fatty acids.

24. The method of claim 23, wherein the subject is cardiopathic.

25. The method of claim 23, wherein the subject is affected by coronary ischemia.

26. The method of claim 23, wherein the subject is affected by cardiac insufficiency.

27. The method of claim 23, wherein the subject is affected by cardiac decompensation.

28. The method of claim 23, wherein the subject is affected by diabetic pathology concomitant with cardiopathy.

29. A method of treating atrial fibrillation, comprising administering to a subject in need thereof an effective amount of an oral dosage form comprising 500-1000 mg of ω-3 fatty acids comprising ω-3 fatty acid ethyl esters in an amount of at least 90% by weight of total fatty acids, wherein the ω-3 fatty acid ethyl esters includes a mixture of EPA ethyl ester and DHA ethyl ester in an amount of at least 80% by weight of total fatty acids.

30. The method of claim 29, wherein the subject is cardiopathic.

31. The method of claim 29, wherein the subject is affected by coronary ischemia.

32. The method of claim 29, wherein the subject is affected by cardiac insufficiency.

33. The method of claim 29, wherein the subject is affected by cardiac decompensation.

34. The method of claim 29, wherein the subject is affected by diabetic pathology concomitant with cardiopathy.

* * * * *